United States Patent [19]

Hupfer et al.

[11] Patent Number: 4,677,230
[45] Date of Patent: Jun. 30, 1987

[54] PREPARATION OF 2-METHYL-2-ALKENALS

[75] Inventors: Leopold Hupfer, Friedelsheim; Franz Merger, Frankenthal; Franz J. Broecker, Ludwigshafen; Rolf Fischer, Heidelberg, all of Fed. Rep. of Germany

[73] Assignee: BASF Aktiengesellschaft, Ludwigshafen, Fed. Rep. of Germany

[21] Appl. No.: 872,965

[22] Filed: Jun. 11, 1986

[30] Foreign Application Priority Data

Jun. 28, 1985 [DE] Fed. Rep. of Germany ....... 3523181

[51] Int. Cl.$^4$ .................. C07C 45/67; C07C 45/61
[52] U.S. Cl. .................... 568/450; 568/458; 568/462
[58] Field of Search ............. 568/462, 458, 450

[56] References Cited

U.S. PATENT DOCUMENTS

| | | | |
|---|---|---|---|
| 4,124,619 | 11/1978 | Fitton et al. | 260/410.6 |
| 4,288,643 | 9/1981 | Weber et al. | 568/324 |
| 4,317,945 | 3/1982 | Bernhagen et al. | 568/853 |
| 4,599,458 | 7/1986 | Fischer et al. | 568/450 |
| 4,605,779 | 8/1986 | Matsuda et al. | 568/450 |

FOREIGN PATENT DOCUMENTS

| | | | |
|---|---|---|---|
| 2917779 | 6/1980 | Fed. Rep. of Germany | 568/462 |
| 1310143 | 3/1973 | United Kingdom | 568/462 |

*Primary Examiner*—Werren B. Lone
*Attorney, Agent, or Firm*—John H. Shurtleff

[57] ABSTRACT

2-Methyl-2-alkenals of the formula

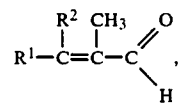

where $R^1$ and $R^2$ are each hydrogen, alkyl which may additionally carry aromatic radicals, or an aromatic radical, are prepared by isomerizing a 2-alkylacrolein of the formula

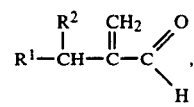

in the presence of hydrogen and of a catalyst which contains palladium and an oxide or salt of a rare earth metal as active components, at from 20° to 120° C. and under from 1 to 100 bar.

14 Claims, No Drawings

PREPARATION OF 2-METHYL-2-ALKENALS

The present invention relates to a process for the preparation of 2-methyl-2-alkenals by isomerizing a 2-alkylacrolein in the presence of hydrogen and of a catalyst which contains palladium and compounds of the rare earth metals as active components.

It is known that 2-alkylacroleins, such as isopropyl- or sec-butylacrolein, can be hydrogenated with hydrogen, in the presence of palladium on active carbon as a carrier, at 100° C. and under 20 bar, to give the corresponding saturated aldehydes (German Laid-Open Applications DOS No. 2,917,779, Example 1b, and DOS No. 2,933,919, Example 1c):

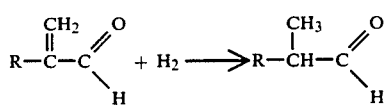

(R = isopropyl or sec-butyl)

It is also known that 2-alkyl-2-alkenals, such as 2-ethyl-2-hexenal, can be reacted with hydrogen in the presence of palladium on $SiO_2$ at 90° C. and under 200 bar to give 2-ethylhexanal (German Laid-Open Application DOS No. 1,941,634, Example 1):

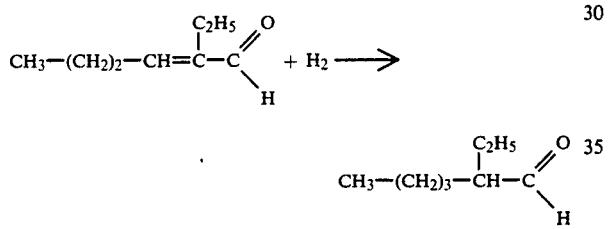

Instead of palladium catalysts, supported catalysts which contain not only palladium but also oxides of rare earths, such as praseodymium oxide or cerium dioxide, can particularly advantageously be used in this hydrogenation (European Pat. No. 8,022). German Laid-Open Application DOS No. 2,621,224 (Example 11) states that acetoxyethylacrolein can be isomerized to 2-methyl-4-acetoxy-2-butenal in the presence of a catalyst which consists of palladium (5% by weight), tetramethylthiourea and carbon and in the presence of hydrogen at 100° C. and under atmospheric pressure, in xylene as the solvent.

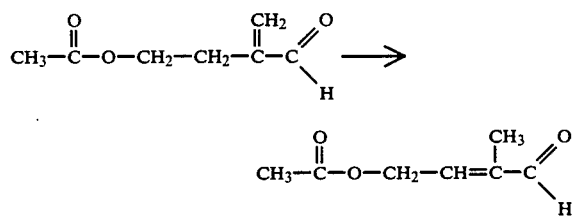

It is an object of the present invention to provide a process which permits 2-alkylacroleins, which are readily obtainable from alkanals and formaldehyde, to be isomerized to 2-methyl-2-alkenals.

We have found that this object is achieved, and that 2-methyl-2-alkenals of the formula

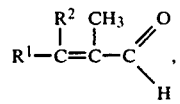

where $R^1$ and $R^2$ are each hydrogen, alkyl of 1 to 18 carbon atoms which may additionally carry aromatic radicals, or an aromatic radical, can be particularly advantageously prepared, if a 2-alkylacrolein of the formula

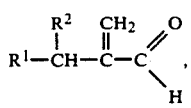

where $R^1$ and $R^2$ have the above meanings, is treated with hydrogen in the presence of a catalyst which contains palladium and an oxide or salt of a rare earth metal as active components, at from 20° to 120° C., in particular from 50° to 100° C., and under from 1 to 100, in particular from 1 to 20, bar.

The formation of 2-methyl-2-alkenals of the formula I as principal products of the novel process is surprising since it is known that both the 2-alkylacroleins of the formula II and the 2-methyl-2-alkenals of the formula I, which are the desired reaction products in the isomerization, can be hydrogenated to the saturated alkanals. It could not be foreseen that, under the conditions of the novel process, the isomerization would take place at an adequate rate or the hydrogenation, on the other hand, would occur to a substantially smaller extent.

If the isomerization of 2-ethylacrolein to tiglinaldehyde (trans-2-methyl-2-butenal) is used as an example, the novel process may be represented by the following equation:

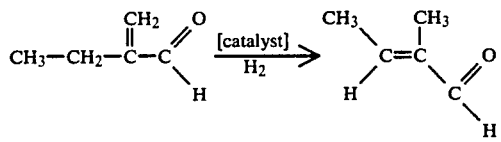

2-Methylbutanal occurs as a by-product, being formed by hydrogenation of 2-ethylacrolein and tiglinaldehyde.

The acrolein derivatives of the formula II which are used as starting materials contain, as radicals $R^1$ and $R^2$, hydrogen, alkyl of 1 to 18, preferably 1 to 12, carbon atoms which may be substituted by aromatic radicals, or aromatic radicals. Alkyl is, for example, methyl, ethyl, n-propyl, isopropyl, n-butyl, isobutyl, tert-butyl, pentyl, hexyl, nonyl, decyl or dodecyl. Examples of aromatic radicals are phenyl radicals which may furthermore contain substituents such as alkyl, alkoxy or halogen. Examples of compounds of the formula II are 2-ethylacrolein, 2-n-butylacrolein, 2-isopropylacrolein, 2-n-propylacrolein, 2-decylacrolein, 2-n-pentylacrolein, 2-benzylacrolein, 2-heptylacrolein, 2-n-hexylacrolein, 2-isobutylacrolein and 2-nonylacrolein. The starting compounds of the formula II can be prepared, for example, by reacting an alkanal with formaldehyde and a secondary amine in the presence of a carboxylic acid (German Laid-Open Application DOS No.3,106,557).

The catalysts in whose presence the novel reaction is carried out contain palladium or platinum and an oxide or salt of a rare earth metal as active components. Examples of suitable catalysts are the catalysts described in European Pat. No. 8,022, whose active components consist of from 2 to 90% by weight of palladium and from 10 to 98% by weight of an oxide or salt of a rare earth metal or of a mixture of different oxides and/or salts of this type. In addition to palladium, all oxides and salts of the rare earth metals (referred to below as RE compounds) are suitable catalytically active additives, but mainly the oxides, in particular lanthanum oxide ($La_2O_3$), samarium oxide ($Sm_2O_3$), gadolinium oxide ($Gd_2O_3$) and holmium oxide ($Ho_2O_3$), and especially cerium oxide ($CeO_2$), praseodymium oxide ($Pr_2O_3$) and neodymium oxide ($Nd_2O_3$).

Instead of the oxides, it is also possible to use the salts of the rare earth metals, for example the nitrates, sulfates, phosphates, chlorides and carbonates. Toluenesulfonates and in particular the organic salts of the higher fatty acids, e.g. stearic acid, are preferred. If the salts are soluble in the starting compound to be hydrogenated, they may be mixed with this before the reaction, so that it is only necessary to pass the mixture over a palladium catalyst. This process is advisable particularly where it is desired to carry out the hydrogenation over an existing conventional palladium catalyst. By changing over to the isomerization according to the invention, the expense of a catalyst change is avoided. In this case, the product need only be distilled off from the RE salt.

Moreover, it is not necessary to use the pure RE compounds; mixtures of these are just as suitable, for example the commercial oxides and salts of technical purity, which contain, for example, only 90% by weight of the pure RE compound, the remainder consisting of several other accompanying RE compounds.

Since on the simultaneous presence of the two components of the catalyst, i.e. the palladium on the one hand and the RE compound on the other hand, is essential in the novel process the action desired according to the invention occurs even when the palladium and the RE compound are present together in a suspension of the aldehyde to be hydrogenated or in an organic solution of this aldehyde. This is also true, for example, for a suspension of a Pd supported catalyst (for example with active carbon as the carrier) and an RE oxide supported catalyst (for example with alumina as the carrier).

Such procedures are possible in principle and are frequently also suitable for hydrogenation on the laboratory scale or pilot scale. However, for continuous industrial operation, it is advisable, for well known reasons relating to process engineering, to arrange the catalyst as a fixed bed in a reactor column and to pass hydrogen and the aldehyde or a solution of the aldehyde over such a fixed bed.

For this purpose, it is preferable to use a supported catalyst on which both the palladium and the RE compound have been applied. Such supported catalysts can be prepared by impregnating the carrier with an aqueous solution which contains a Pd salt, such as palladium nitrate, and an RE salt in an appropriate ratio, drying the product and heating it in a stream of air, the RE oxide being formed. Although the Pd metal is formed automatically under the hydrogenating conditions, it is also possible to subject the supported catalyst to a separate hydrogenation for this purpose. Examples of suitable carriers are active carbons, alumina and silica gel in the form of pellets, granules, spheres or extrudates having diameters of from 2 to 20 mm and a length of from 5 to 50 mm. Depending on the three-dimensional form and total surface area of the carrier, a bed comprising 1 liter of such supported catalysts contains about 4-80 g of active catalyst components. In general, the weight ratio of Pd to the RE compound is from 2:98 to 90:10, but is preferably from 20:80 to 80:20.

The isomerization can be carried out batchwise or continuously, as a fixed bed reaction, for example in the liquid phase or by the trickle-bed procedure, or using a suspended catalyst. The reaction temperatures are from 20° to 120° C., in particular from 50° to 100° C. The pressures required are from atmospheric pressure to 100 bar, in particular from 1 to 20 bar. To promote isomerization and achieve an adequate reaction rate, in general a fairly low pressure is used in conjunction with a high reaction temperature, and a higher reaction pressure with a lower reaction temperature.

In a preferred embodiment of the process, the isomerization is carried out in a solvent which is inert under the reaction conditions. Examples of solvents of this type are $C_5$-$C_8$-paraffins, cyclic hydrocarbons, such as cyclohexane, methylcyclohexane, toluene or xylenes, alcohols, such as methanol or ethanol, cyclic ethers, such as tetrahydrofuran or dioxane, and esters, such as methyl or ethyl acetate. The amount of solvent is not critical and can be, for example, from 0.5 to 10 times the weight of the aldehyde.

The process according to the invention has advantages over the conventional processes for the preparation of 2-methyl-2-alkenals. For example, particularly in the synthesis of 2-methyl-2-alkenals having an odd number of carbon atoms, aldol condensation of two different aldehydes gives only low yields. The synthesis of tiglinaldehyde from acetaldehyde and propionaldehyde takes place with a yield of, for example, only 30% (J. Prakt. Chem. 155, 310–316). In contrast, alkenals can be reacted with formaldehyde to give 2-alkylacroleins in high yields (German Laid-Open Application DOS No. 3,106,557), and the 2-alkylacroleins can then be isomerized to 2-methyl-2-alkenals by the novel process. The 2-methylalkanals obtained as by-products in the process according to the invention are also useful intermediates which can be oxidized to the corresponding carboxylic acids.

The 2-methyl-2-alkenals (I) obtainable by the novel process are useful intermediates for the preparation of dyes, drugs and crop protection agents. They are also used as aromas (German Pat. No. 2,927,090).

EXAMPLE 1

25 g of a catalyst containing palladium and cerium (0.08% of PdO and 0.61% of $CeO_2$ on 4 mm $\gamma$-$Al_2O_3$ extrudates), mixed with 5 mm glass rings, were introduced into a vertical glass reactor tube (150 ml) and activated with about 3 l hour of hydrogen for 16 hours at 180° C.

A solution of 60 g of 2-ethylacrolein in 240 g of dioxane was pumped over the catalyst at 100±20° C., using the trickle-bed procedure. The solution was collected in a 500 ml flask provided with a jacketed coil condenser and was recycled from there over the catalyst, the rate of circulation being about 20 liters per hour. 6 liters/hour of hydrogen were passed in at the upper end of the reactor tube filled with catalyst. Waste gas was removed via the water-cooled jacketed coil condenser. About every two hours, samples of the reaction mixture were taken and investigated by gas chromatography to determine their content of the ethylacrolein employed, tiglinaldehyde (trans-2-methyl-2-butenal) formed and 2-methylbutanal (Table 1).

TABLE 1

Preparation of tiglinaldehyde by isomerization of ethylacrolein over Pd/Ce/Al$_2$O$_3$ catalysts

| Reaction time [h] | GC analysis (% by area)[1] | | | |
|---|---|---|---|---|
| | 2-Ethyl-acrolein | Tiglin-aldehyde | 2-Methyl-butanal | Dimeric[2] 2-ethyl-acrolein |
| 0.1 | 91.8 | 3.1 | 0.6 | 1.4 |
| 2 | 57.4 | 26.6 | 8.0 | 1.4 |
| 4 | 27.8 | 51.3 | 16.0 | 1.7 |
| 5.5 | 10.1 | 62.7 | 20.8 | 1.6 |
| 6.5 | 2.1 | 67.3 | 24.1 | 1.4 |

[1]Carbowax 20 M column, 4 m, isothermal for 4 minutes at 100° C., followed by a temperature program from 100 to 200° C. at 10° C. per minute.
[2]2,5-Diethyl-2-formyl-2,3-dihydro-4H—pyran.

After 6.5 hours, virtually all the acrolein had been converted, and the reacted mixture (255 g) was worked up by distillation in a spinning band column. In the mixture initially distilled off and consisting of dioxane, ethylacrolein and 2-methylbutanal, quantitative GC analysis indicated the presence of 1.1 g (2%, based on ethylacrolein used) of ethylacrolein and 13.3 g (22%, based on ethylacrolein used) of 2-methylbutanal. Finally, 28.2 g (47%, based on ethylacrolein used) of tiglinaldehyde of boiling point 114°–116° C./1000 mbar were obtained. According to GC analysis, the distillation residue (5.5 g of oil) contained 2,5-diethyl-2-formyl-2,3-dihydro-4H-pyran.

EXAMPLE 2

The procedure described in Example 1 was used, and 125 g of Pd/Ce/Al$_2$O$_3$ catalyst were activated and reacted initially for 3 hours at 50±2° C. with 270 g of ethylacrolein. 6 liters/hour of hydrogen were passed in. Table 2 shows the changes in concentrations in the reaction mixture as a function of the reaction time.

TABLE 2

Preparation of tiglinaldhyde by isomerization of ethylacrolein over Pd/Ce/Al$_2$O$_3$ catalysts

| Reaction time [h] | GC analysis (% by area) | | | |
|---|---|---|---|---|
| | 2-Ethyl-acrolein | Tiglin-aldehyde | 2-Methyl-butanal | Dimeric 2-ethyl-acrolein |
| 0.1 | 81.1 | 1.6 | 2.2 | |
| 1 | 69.6 | 9.6 | 7.7 | |
| 2 | 57.9 | 16.7 | 13.0 | |
| 3 | 46.6 | 23.5 | 18.3 | |
| 4 | 49.7 | 27.0 | 15.5 | |
| 5.5 | 29.8 | 39.0 | 20.1 | |
| 7.25 | — | 51.8 | 37.5 | 2.4 |

According to quantitative gas chromatographic analysis, the molar ratio of tiglinaldehyde to 2-methylbutanal was 1.1:1.

EXAMPLE 3

Similarly to Example 1, the reactor was charged with 160 g of Pd/Pr$_2$O$_3$ catalyst (0.5% of Pd and 5% of Pr$_2$O$_3$ on γ-Al$_2$O$_3$ as the carrier) and operated at 50° C., using 220 g of ethylacrolein and 6 liters of hydrogen per hour. After six hours, virtually all of the ethylacrolein had been converted. According to quantitative gas chromatographic analysis, the molar ratio of tiglinaldehyde to 2-methylbutanal was 0.77:1 at this point.

EXAMPLE 4

As described in Example 1, 125 g of palladium/CeO$_2$/Al$_2$O$_3$ catalyst were activated and reacted with 280 g of n-hexylacrolein, initially for 4 hours at 50±2° C. and then for 3 hours at 100±2° C. 6 liters/hour of hydrogen were passed in. After 7 hours, virtually all of the n-hexylacrolein had been converted. The molar ratio of 2-methyl-2-octenal to 2-methyloctanal was 0.63:1. Fractional distillation of 110 g of the reacted mixture gave 57.3 g of 2-methyloctanal of boiling point 79° C./30 mbar ($n_D^{20}$ = 1.4200) and 35.7 g of 2-methyl-2-octenal of boiling point 92° C./30 mbar ($n_D^{20}$ = 1.4555).

EXAMPLE 5

As described in Example 1, 25 g of palladium/CeO$_2$/Al$_2$O$_3$ catalyst were activated, and reacted with a solution of 60 g of n-nonylacrolein in 240 g of dioxane at 100±2° C. for 8 hours. 6 liters/hour of hydrogen were passed in. After 8 hours, the reaction mixture contained only 4.5% of n-nonylacrolein. According to quantitative gas chromatographic analysis, the molar ratio of 2-methyl-2-undecenal to 2-methylundecanal was 0.35:1.

EXAMPLE 6

950 ml (670 g) of a catalyst containing palladium and cerium (0.08% of PdO and 0.61% of CeO$_2$ on 4 mm γ-Al$_2$O$_3$ extrudates) were activated with hydrogen at 180° C. for 24 hours in a 1 l hydrogenation autoclave. 100 ml/hour of 2-ethylacrolein were then pumped over the catalyst for 24 hours at 50° C., and a hydrogen pressure of 2 bars using the trickle-bed procedure. Some of the liquid was recycled over the catalyst. The mixture discharged from the hydrogenation autoclave and collected in the course of 24 hours had the following composition: 53.6% of tiglinaldehyde, 29.1% of 2-methylbutanal and 12.1% of unconverted 2-ethylacrolein.

We claim:

1. A process for the preparation of a 2-methyl-2-alkenal of the formula

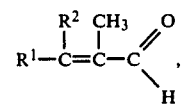

where R$^1$ and R$^2$ are each hydrogen, alkyl of 1 to 18 carbon atoms which may additionally carry aromatic radicals, or an aromatic radical, wherein a 2-alkylacrolein of the formula

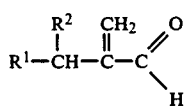

where R$^1$ and R$^2$ have the above meanings, is treated with hydrogen in the presence of a catalyst which contains palladium and an oxide or salt of a rare earth metal as active components, at from 20° to 120° C. and under a pressure from 1 to 100 bar.

2. A process as claimed in claim 1, wherein the active material of the catalyst consists of from 2 to 90% by weight of palladium and from 10 to 98% by weight of an oxide or salt of a rare earth metal.

3. A process as claimed in claim 1, wherein the catalyst used is a supported catalyst which contains from 0.01 to 10% by weight of palladium and from 0.01 to 20% by weight of an oxide or salt of a rare earth metal.

4. A process as claimed in claim 3, wherein the supported catalyst contains active carbon, alumina or silica as the carrier.

5. A process as claimed in claim 1, wherein the treatment is carried out at from 50° to 100° C. and under a pressure from 1 to 20 bar.

6. A process as claimed in claim 1, which is carried out in the presence of a solvent which is inert under the reaction conditions.

7. A process as claimed in claim 1, wherein, in the 2-alkylacrolein of the formula II, $R^1$ and $R^2$ are each hydrogen or alkyl of 1 to 12 carbon atoms.

8. A process as claimed in claim 1 wherein $R^1$ and $R^2$ are each hydrogen, alkyl of 1 to 12 carbon atoms or an aromatic radical.

9. A process for the preparation of a 2-methyl-2-alkenal of the formula $$R^1-\underset{\underset{H}{|}}{C}=\underset{\underset{}{\overset{CH_3}{|}}}{C}-C\overset{\displaystyle O}{\underset{\displaystyle H}{\diagup\!\!\!\diagdown}} \quad \text{I}$$

where $$R^1-\underset{\underset{}{\overset{R^2}{|}}}{C}=$$

is alkylene of 1 to 10 carbon atoms or benzylidene, which process comprises:

reacting a 2-alkylacrolein of the formula $$R^1-\underset{\underset{}{\overset{R^2}{|}}}{CH}-\underset{\underset{}{\overset{CH_2}{||}}}{C}-C\overset{\displaystyle O}{\underset{\displaystyle H}{\diagup\!\!\!\diagdown}} \quad \text{II}$$

where $$R^1-\underset{\underset{}{\overset{R^2}{|}}}{CH}-$$

is alkyl of 1 to 10 carbon atoms or benzyl, with hydrogen in the presence of a catalyst which contains palladium and an oxide or salt of a rare earth metal as active components, at from 20° to 120° C. and under a pressure from 1 to 100 bar.

10. A process as claimed in claim 9 wherein the 2-alkylacrolein of the formula II is selected from the group consisting of 2-ethylacrolein, 2-n-butylacrolein, 2-isopropylacrolein, 2-n-propylacrolein, 2-decylacrolein, 2-n-pentylacrolein, 2-benzylacrolein, 2-heptylacrolein, 2-n-hexylacrolein, 2-isobutylacrolein and 2-nonylacrolein.

11. A process as claimed in claim 9 wherein the active material of the ctalyst consists of from 2 to 90% by weight of palladium and from 10 to 98% by weight of an oxide or salt of a rare earth metal.

12. A process as claimed in claim 9 wherein the catalyst used is a supported catalyst which contains from 0.01 to 10% by weight of palladium and from 0.01 to 20% by weight of an oxide or salt of a rare earth metal.

13. A process as claimed in claim 12 wherein the supported catalyst contains active carbon, alumina or silica as the carrier.

14. A process as claimed in claim 13 wherein the reaction is carried out at from 50° to 100° C. and under a pressure from 1 to 20 bar.

* * * * *